United States Patent [19]

Myoken et al.

[11] Patent Number: 5,110,737
[45] Date of Patent: May 5, 1992

[54] METHOD FOR THE ISOLATION OF HYBRIDOMAS USING CHOLESTEROL AUXOTROPHY OF MYELOMA CELLS

[75] Inventors: Yoshinari Myoken, Lake Placid, N.Y.; Tetsuji Okamoto, Hiroshima, Japan; J. Denry Sato, Lake Placid, N.Y.

[73] Assignee: W. Alton Jones Cell Science Center Incorporated, Lake Placid, N.Y.

[21] Appl. No.: 388,048

[22] Filed: Jul. 31, 1989

[51] Int. Cl.$^5$ ............................................. C12N 5/00
[52] U.S. Cl. ......................... 435/240.27; 435/240.31; 435/240.2; 435/70.2; 435/240.3; 435/240.21
[58] Field of Search ............... 435/70.2, 70.21, 240.27, 435/240.26, 240.1, 240.3, 240.31

[56] References Cited

U.S. PATENT DOCUMENTS 2,787,581  4/1957  Scherr .................................. 435/32

OTHER PUBLICATIONS

Myoken et al. "A New Method for the Isolation of NS-1 Hybridomas Using Cholesterol Auxotrophs of NS-1 Myeloma Cells", *Fourth International Cell Biology Congress*, Montreal, Canada, Aug. 14–19, 1988.
Leonard et al, *Biochem. Biophys. Acta* 947:101–112 (1988).
Perlman, D., *Meth. Enzymol.* 58:110–116 (1979).
Sigma Catalog, 1991, p. 169.

*Primary Examiner*—Douglas W. Robinson
*Assistant Examiner*—Jane A. Williams
*Attorney, Agent, or Firm*—Browdy and Neimark

[57] ABSTRACT

Cholesterol auxotrophy of myeloma cells is used as the basis for selecting hybridomas. The outgrowth of nascent hybridomas in a cholesterol-free medium was 3- to 9-fold more efficient than that in HAT medium and resulted in 3- to 13-times as many antigen-reactive hybridoma cells. This method of hybridoma selection can be applied with any sterol-dependent parent cell line. The nutrient medium is also preferably free of Ham's F-12 nutrient mixture.

11 Claims, 7 Drawing Sheets

METHOD FOR THE ISOLATION OF HYBRIDOMAS USING CHOLESTEROL AUXOTROPHY OF MYELOMA CELLS

This invention was made with Government support under NCI grant No. R01 CA40294 awarded by the National Cancer Institute. The Government has certain rights in the invention.

FIELD OF THE INVENTION

The present invention relates generally to hybridoma selection, and more particularly to hybridoma selection using a cholesterol-free culture medium.

BACKGROUND OF THE INVENTION

Since the inception of the hybridoma technology developed by Kohler and Milstein, selection of successful hybridoma clones has been based on the selective outgrowth of hybrid cells in HAT (hypoxanthine/aminopterin/thymidine) selection medium. This prior art selection technique relies on inhibition of a synthetic pathway in the myeloma for the production of a necessary metabolite. A myeloma cell line which is deficient in hypoxanthine phosphoribosyl transferase (HPRT) is used as the fusion partner with the mammalian cell of interest. Such a mutant cell line, having no purine salvage pathway enzymes, cannot grow in HAT medium as aminopterin is an antagonist of dihydrofolate reductase and thus blocks the primary synthetic pathway. An unblocked alternative (or salvage) synthetic pathway, inherited from the mammalian fusion partner of the myeloma, exists in the hybridoma. Thus, the blockage of the synthetic pathway kills unfused myeloma cells, but not fused hybridomas, which are capable of using the necessary metabolite by an alternative pathway.

This technique, however, suffers certain drawbacks as aminopterin is inherently highly toxic to mammalian cells. Modified protocols for selecting hybridomas derived from HPRT-deficient cells have been described in which aminopterin has been replaced by the less toxic methotrexate or in which aminopterin and thymidine have been omitted in favor of azaserine. These modified selection techniques, however, still rely on inhibition of synthetic pathways in myelomas for the production of a necessary metabolite.

Unfortunately, inhibition of synthetic pathways requires the addition to the culture medium of a substance which is non-essential for cell growth. The substance can inhibit the growth of myeloma cells in ways additional to the blockage of the specified synthetic pathway and can thus inhibit the growth of fused hybridomas. Further, some of these substances have resulted in chromosomal instability. Thus, there has been an effort to develop selection media which do not rely upon inhibition of a synthetic pathway.

As noted in a paper from the laboratory of the present inventors, (Sato, J.D. et al "Cholesterol Requirement of NS-1 Mouse Myeloma Cells for growth in Serum-Free Medium", *Mol. Biol. Med.*, 2, 121-134 (1984)), NS-1-Ag4-1 (NS-1) mouse myeloma cells, but not NS-1 hybridomas, require exogenous cholesterol for growth in serum-free medium owing to an inability to convert lanosterol to cholesterol. Based on this phenotype of cholesterol auxotrophy, it was speculated, in that paper, that cholesterol-free serum-free (CFSF) medium could be used as an alternative to HAT medium as a selective agent for NS-1 hybridomas. P3-X63-Ag8 and X63-Ag8.653 myeloma cells have the same phenotype of cholesterol auxotrophy. That paper specifically described the growth characteristics of myeloma cells in a cholesterol-free and serum-free medium supplemented with Ham's F-12 nutrient mixture. Yet, because it was unknown whether or to what extent the hybridomas would release cholesterol into the surrounding medium where it would become available for the auxotrophic myeloma cells and thus prevent selection, that paper failed to provide a reasonable expectation of success, let alone an expectation of greatly superior selection capability as compared to HAT selection.

In a later paper from the laboratory of the present inventors (J. D. Sato, T. Kawamoto, and T. Okamoto (1987), J. Exp. Med. 165: 1761-1766), the growth of myelomas in a cholesterolfree, serum-free medium lacking Ham's F-12 nutrient mixture was described, but there was no suggestion in that paper of the use of the described medium for hybridoma selection. Moreover, the growth of myelomas in the F-12 supplemented medium was not compared to the growth of myelomas in the same medium lacking F-12. At that time those skilled in the art would have expected that these growth characteristics would have been similar in each medium.

SUMMARY OF THE INVENTION

It is an object of the present invention to provide a method for hybridoma selection which avoids the above noted drawbacks of the prior art.

It is another object of the present invention to provide a method for hybridoma selection which does not rely on the addition of metabolic inhibitors to the culture medium.

It is a further object of the present invention to provide a method for hybridoma selection with improved outgrowth of hybridomas.

These and other objects are accomplished by the present invention. Hybridoma cells which are the hybridization product of a myeloma cell which is a cholesterol auxotroph and an antibody producing cell which is capable of synthesizing cholesterol, may be selected from a mixture of such cells and the unfused myeloma parent cells by culturing in a nutrient medium which is essentially free of cholesterol and cholesterol precursors, and which preferably is also essentially free of Ham's F-12 nutrient mixture. It has been unexpectedly discovered that a much higher percent of antibody producing hybridomas is obtained upon selection by means of the present invention as compared to the prior art HAT technique.

μg/ml), insulin (5 μg/ml), ethanolamine (10 μM), mercaptoethanol (10 μM), selenium (as Na salt) (2.5 nM), and LDL (5 μg/ml). The seeding density was $1 \times 10^4$ cells/well and the resulting cells were counted after 126 hours.

Figure 3:
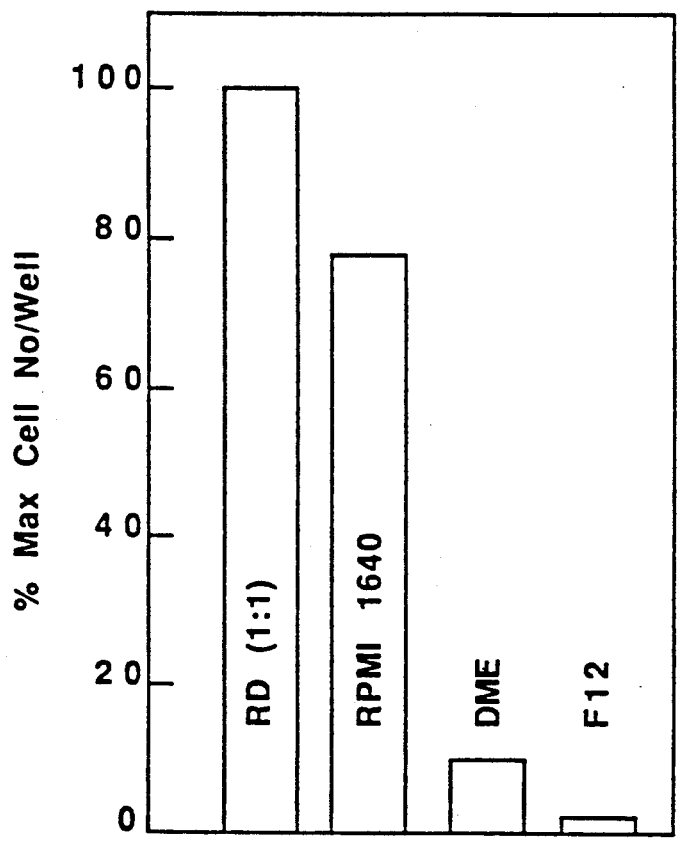
FIG. 3 graphically compares NS-1 myeloma growth in mediums RD (a 1:1 mixture of RPMI 1640 and DME), RPMI 1640, Dulbecco's modified Eagle's medium (DME) and Ham's F-12 nutrient medium, each medium including 5F, i.e., transferrin ($Fe^{3+}$-free) (10
Figure 4:
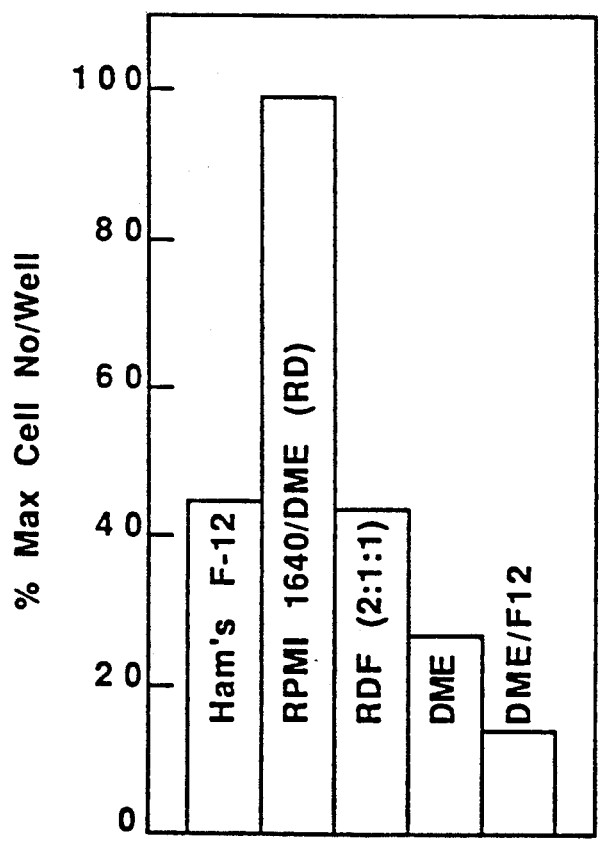
Figure 5:
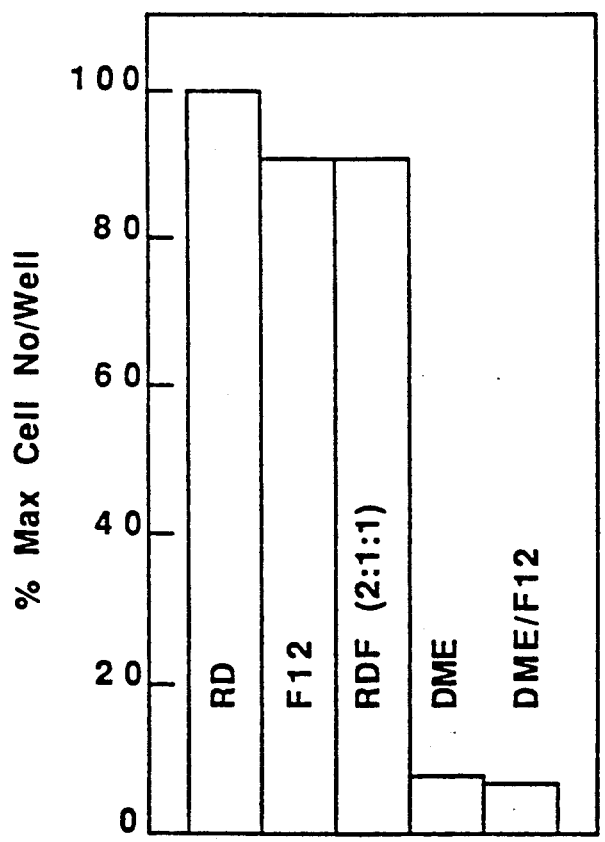

FIGS. 4 and 5 are similar to FIG. 3, but are based upon the growth of NS-hybridomas 455 and 528, respectively, after 112 hrs.

Figure 6:
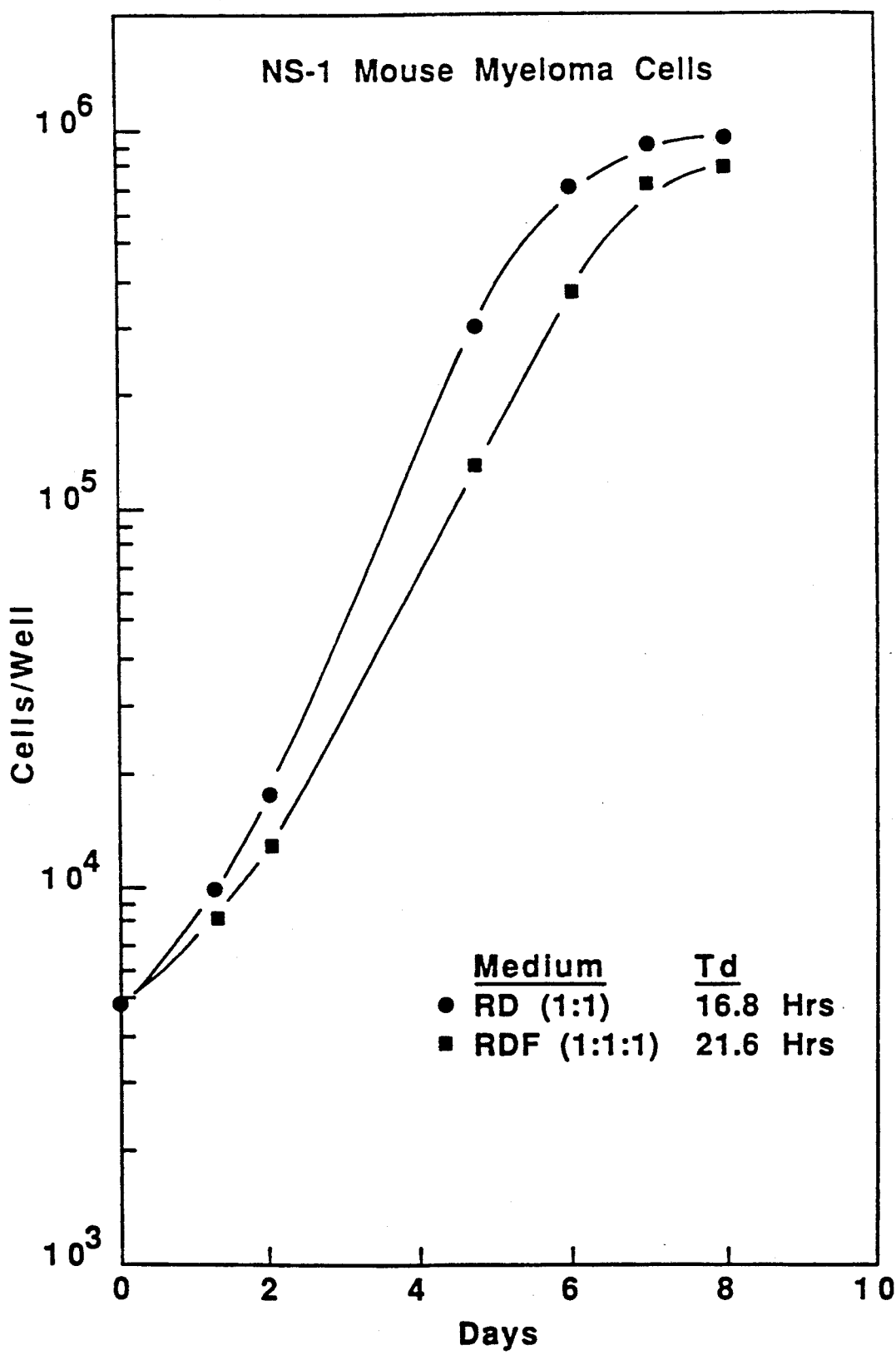
Figure 7:
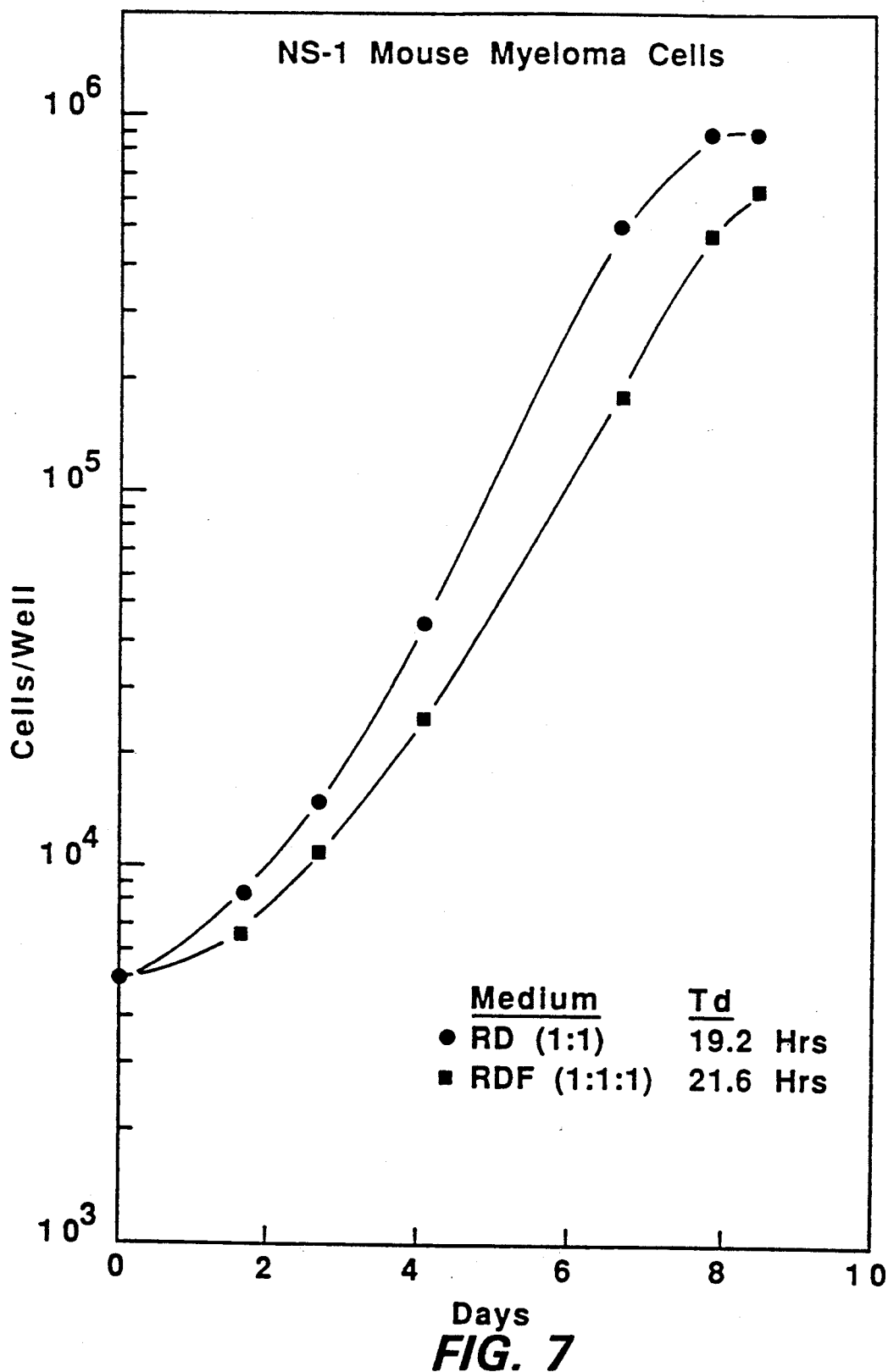

FIGS. 6 and 7 graphically compare myeloma growth in RD (•) and RDF(■) (which in a 1:1:1 mixture of RPMI 1640, DME and Ham's F-12 nutrient mixture). Each medium was supplemented with 5F and LDL as indicated for FIG. 4. The seeding density was $5 \times 10^3$ cells per well.

DETAILED DESCRIPTION OF PREFERRED EMBODIMENTS

The medium for use in the present invention should lack amounts of cholesterol sufficient to support significant growth of auxotrophic myeloma parents. In addition, it should be such amounts of any cholesterol precursors produced downstream from the deficient essential enzyme in the metabolic pathway of cholesterol production of the myeloma parent cells. Thus, if the myeloma parent cells are NS-1 cells which lack 3-ketosteroid reductase, the medium should contain no cholesterol precursors which are produced in the cholesterol synthetic pathway downstream of the 3-ketosteroid reductase. Because serum contains cholesterol, the medium should also be serum-free, but the use of cholesterol-free serum is permissible.

The medium may be supplemented with fatty acid-free albumin, such as BSA, and a source of fatty acid, such as linoleic acid and/or oleic acid, in amounts effective to sustain hybridoma growth.

The cholesterol-free medium should also preferably contain no more than insignificant amounts of substances, including mixtures, which inhibit the growth of the parent myeloma, such as Ham's F-12 nutrient mixture.

Ham's F-12 nutrient mixture has the following composition, as used in powder or liquid form (the prior art publication used powdered F-12):

| F-12 Nutrient Mixture (Ham)[1] | | |
|---|---|---|
| COMPONENT | 1X Liquid mg/L | Powder mg/L |
| INORGANIC SALTS: | | |
| CaCl₂ (anhyd.) | — | 33.22 |
| CaCl₂.2H₂O | 44.00 | — |
| *CuSO₄.5H₂O | 0.00249 | 0.00249 |
| *FeSO₄.7H₂O | 0.834 | 0.834 |
| KCl | 223.60 | 223.60 |
| KH₂PO₄ | — | — |
| MgCl₂ (anhyd.) | — | 57.22 |
| MgCl₂.6H₂O | 122.00 | — |
| MgSO₄ (anhyd.) | — | — |
| MgSO₄.7H₂O | — | — |
| NaCl | 7599.00 | 7599.00 |
| NaHCO₃ | 1176.00 | — |
| Na₂HPO₄ (anhyd.) | — | 142.04 |
| Na₂HPO₄.7H₂O | 288.00 | — |
| *ZnSO₄.7H₂O | 0.863 | 0.863 |
| OTHER COMPONENTS: | | |
| D-Glucose | 1802.00 | 1802.00 |
| *Hypoxanthine | 4.10 | — |
| *Hypoxanthine (sodium salt) | — | 4.77 |
| *Linoleic acid | 0.084 | 0.084 |
| *Lipoic acid | 0.21 | 0.21 |
| Phenol red | 1.20 | 1.20 |
| *Putrescine.2HCl | 0.161 | 0.161 |

| F-12 Nutrient Mixture (Ham)[1] | | |
|---|---|---|
| COMPONENT | 1X Liquid mg/L | Powder mg/L |
| Sodium pyruvate | 110.00 | 110.00 |
| *Thymidine | 0.73 | 0.73 |
| AMINO ACIDS: | | |
| *L-Alanine | 8.90 | 8.90 |
| L-Arginine.HCl | 211.00 | 211.00 |
| L-Asparagine.H₂O | 15.01 | 15.01 |
| L-Aspartic acid | 13.30 | 13.30 |
| L-Cysteine | — | — |
| L-Cysteine.HCl.H₂O | 35.12 | 35.12 |
| L-Glutamic acid | 14.70 | 14.70 |
| L-Glutamine | 146.00 | 146.00 |
| Glycine | 7.50 | 7.50 |
| L-Histidine.HCl.H₂O | 20.96 | 20.96 |
| L-Isoleucine | 3.94 | 3.94 |
| L-Leucine | 13.10 | 13.10 |
| L-Lysine.HCl | 36.50 | 36.50 |
| L-Methionine | 4.48 | 4.48 |
| L-Phenylalanine | 4.96 | 4.96 |
| *L-Proline | 34.50 | 34.50 |
| L-Serine | 10.50 | 10.50 |
| L-Threonine | 11.90 | 11.90 |
| L-Tryptophan | 2.04 | 2.04 |
| L-Tyrosine | 5.40 | — |
| L-Tyrosine (disodium salt) | — | 7.78 |
| L-Valine | 11.70 | 11.70 |
| VITAMINS: | | |
| Biotin | 0.0073 | 0.0073 |
| D-Ca pantothenate | 0.48 | 0.48 |
| Choline chloride | 13.96 | 13.96 |
| Folic acid | 1.30 | 1.30 |
| i-Inositol | 18.00 | 18.00 |
| Niacinamide | 0.037 | 0.037 |
| Pyridoxine.HCl | 0.062 | 0.062 |
| Riboflavin | 0.038 | 0.038 |
| Thiamine.HCl | 0.34 | 0.34 |
| *Vitamin B₁₂ | 1.36 | 1.36 |

[1]Ham, R. G. (1965), Proc. Nat. Acad. Sci., 53, 288

The components components noted with an asterisk (*) are identical or equivalent (e.g., salt) form in DME or RPMI 1640. Thus, it is believed that some, all or a mixture of all of those components may be responsible for the inhibitory effects of the F-12 mixture. Fe, Cu and Zn ions and breakdown products of fatty acids are especially suspected.

The preferred nutrient medium is RD +5F, supplemented with fatty acid-free bovine serum albumin and oleic and/or linoleic acid. The RD +5F medium, and the growth characteristics of various myelomas on this medium, as supplemented, are discussed in Sato et.al., J. Exo. Med., 165, 1761–66 (1987); Sato et.al., FASEB J. 2, A579 (1988) (Abstract); and Sato et.al., In Vitro Cell. Dev. Biol., 24, 1223–28 (1988) all of which are incorporated herein by reference. The growth of NS-1 hybridomas from NS-1 cholesterol auxotrophs, in RDF (including F-12) is described in Sato et.al., Mol. Biol. Med., 2, 121–134 (1984) and Chen et.al., Exp. Cell Research, 163, 117–126 (1986), both of which are also incorporated herein by reference.

The myeloma parent cells should be cholesterol auxotrophs, such as NS-1, NS-0, X63-Ag8 and X63.653 cholesterol auxotrophs. Lines NS-1-Ag4-1, X63-Ag8 and X63-Ag8.653, are known auxotrophs and are preferred. NS-1 hybridomas, especially NS-1Ag4-1, are most preferred. It should be understood, however, that the present invention is applicable to any myeloma parent cell which is a cholesterol auxotroph. While murine cells are exemplified, it should be understood that cholesterol auxotrophic cells from any species (e.g., human, mouse, rat, hamster, guinea pig, etc.) may be used. It can be readily determined, without more than routine experimentation, whether or not any given myeloma line is a cholesterol auxotroph. It is not necessary that the myeloma line be HPRT-deficient.

The fusion partners of the myelomas may be any cells which are capable of synthesizing cholesterol from a cholesterol precursor upstream from the point of the essential enzyme deficiency of the myeloma and which maintain these characteristics when fused with the parent myeloma cell line. While the hybridoma process is primarily used to immortalize antibody-producing cells, it can also be used for the production of any cell product of interest. Thus, while the fusion partner cells are preferably antibody-producing cells, any cell which produces any product both before and after fusion to the myeloma can be used. In particular, mammalian antibody-producing cells, especially spleen cells, are useful. Any other normal mammalian lymphoid cells, such as lymphocytes from blood, tonsils or other sources, may also be used for this purpose. Murine, especially mouse, spleen cells are preferred. No more than routine experimentation is involved for those of ordinary skill in this art to determine whether any given fusion partner possesses these required characteristics.

After fusion is performed in the conventional manner, the fused and unfused cells are transferred to a medium in accordance with the present invention and cultured, usually for about 10–15 days, until the fused hybridomas have sufficiently proliferated and the unfused myeloma cells have died. The unfused normal cells are unable to withstand sustained proliferation in culture (i.e., they are not perpetual) and die as a matter of course. The fused hybridomas may then be harvested, reduced to monoclonality, and further cultured in the conventional manner.

EXAMPLES

The following examples are illustrative only and are not intended as limiting:

(1) Materials and Methods

(a) Culture media

The mouse myeloma line NS-1-Ag4-1 (NS-1), obtained from the American Type Culture Collection (Rockville, MD), was maintained in a humidified atmosphere of 5% $CO_2$ at 37° C. in RD medium supplemented with 5% fetal calf serum (FCS) (MA Bioproducts, Walkersville, MD). RD medium consisted of a 1:1 mixture (by volume) of RPMI 1640 medium (Kyokuto Pharmaceutical Industrial Co., Tokyo, Japan) and Dulbecco's modified Eagle's medium (Kyokuto Pharmaceutical Industrial Co.) to which was added 0.01% sodium pyruvate, 2.2 g/L sodium bicarbonate (all from Wako Chemicals, Osaka, Japan), 15 mM Hepes (Katayama Chemical, Osaka, Japan), and 90 mg/ml kanamycin sulfate (Meiji Pharmaceutical Industrial Co., Tokyo, Japan). RD medium was prepared as described previously (cite).

Cholesterol-free serum-free (CFSF) medium consisted of RD+5F (factor) medium, which contained 10 μg/ml bovine insulin (Sigma Chemical Co., St. Louis, MO), 5 μg/ml human transferrin ($Fe^{3+}$-free), 10 μM 2-mercaptoethanol, 10 μM 2-aminoethanol (all from Sigma Chemical Co.) and 10 nM sodium selenite (Nakarai Chemicals, Kyoto, Japan). This medium was further supplemented with 4 μg/ml oleic acid (Sigma Chemical Co.) complexed with fatty acid-free bovine serum albumin (Pentax, Miles Laboratories, Inc., Naperville, IL) in a 2:1 molar ratio as described previously. Each factor was made as a sterile 100X concentrate and stored at 4° C. NS-1 mouse myeloma cells were monitored for the inability to survive in HAT medium (CFSF medium/HAT/10% FCS). The final concentrations of HAT components were 100 μM hypoxanthine, 0.4 μM aminopterin and 16 μM thymidine.

(b) Production of hybridomas

BALB/c mice were immunized by intraperitoneal administration of $6 \times 10^6$ A431 human epidermoid carcinoma cells three times at fortnightly intervals. Four days after the final immunization, NS-1 cells ($3-6 \times 10^7$) were fused with a 10-fold excess of spleen cells using 42.5% (W/V) polyethylene glycol 2000 (Nakarai Chemicals) supplemented with 15% (W/V) dimethylsulfoxide (Nakarai Chemicals). After fusing, half of the cells were suspended in CFSF medium with or without HT (100 μM hypoxanthine, 16 μM thymidine), and the remaining cells were suspended in HAT medium with or without 10% FCS. One hundred microliters of the suspension of hybrid cells (3x10<NS-1 cells) was seeded in each well of a 96-well microtest plate (Falcon, Oxnard, CA). In an experiment to test the effect of cell density on hybridoma production half of the fusion products were plated in CFSF medium and half were plated in HAT medium in 96-well microtest plates at densities of $3 \times 10^4$, $2 \times 10^4$, $1 \times 10^4$, $5 \times 10^3$, $3 \times 10^3$ and $1 \times 10^3$ NS-1 cells per well. Wells were scored for the presence of hybridoma colonies and A431 reactive antibodies on day 14.

(c) Detection of antibodies by radioimmunoassay

A431-reactive antibodies in hybridoma supernatants were detected with $^{125}I$-labelled rabbit anti-mouse immunoglobulin ($10^5$ cpm/well; Pentax Products, Kankakee, IL) in a known manner. Rabbit anti-mouse immunoglobulin was labelled with Na[$^{125}I$] (Amersham International, Buckinghamshire, England) by the chloramine-T method. Samples having more than twice control levels of radioactivity were scored as positive.

(d) Enzyme-linked immunosorbent assay (ELISA)

Monoclonal antibodies were quantitatively determined by ELISA. Fifty microliters of a hybridoma culture supernatant was added to each well of the 96-well microtest plate coated with goat anti-mouse immunoglobulin (Hyclone Laboratories, Logan UT) and the plate was incubated for 1 hr. After being washed with PBS, each well was incubated with 50 μl of peroxidase-conjugated goat anti-mouse immunoglobulins (Cappel Laboratories, Cochranville, PA) for 1 hr. The plate was then washed extensively, and 100 μl substrate solution containing orthophenylene diamine (0.8 mg/ml) and 0.01% $H_2O_2$ in 50 mM citrate buffer (pH 4.0) were added to each well. After a 10-minute incubation, the enzyme reactions were stopped by addition of 50 μl of 1N HCl. The absorbance of each reaction was measured with a microplate reader (Toso, Tokyo, Japan) at a wavelength of 492 nm.

(2) Results

Table 1 compares the efficiencies of hybridoma production in CFSF medium and in HAT medium. The proportion of wells positive for hybridoma colonies in CFSF medium was approximately 95% while the proportion of positive wells in HAT medium was about 50%. In addition the number of colonies per well was approximately 3-fold higher in CFSF medium than in HAT medium. The frequency of hybridomas, relative to the number of NS-1 cells fused, was $1.3-1.5 \times 10^{-4}$ in CFSF medium while that in HAT medium was $0.3-0.4 \times 10^{-4}$. Thus, hybridoma selection in CFSF medium yielded more than three times as many hybridomas as selection in HAT medium. When tested by radioimmunoassay for antibodies to A431 cells, nearly 50% of the hybridoma wells in CFSF medium were positive while only 12% of the hybridoma wells in HAT medium were positive. The addition of hypoxanthine and thymidine (HT) to CFSF medium did not markedly affect the outgrowth of nascent hybridomas.

These results show great superiority to the conventional HAT selection process, which superiority is highly unexpected and unobvious.

TABLE 1

Hybridoma Growth in CFSF Medium and Hat Medium[a]

| Medium | Positive Wells (%) | Mean Colonies/Well | Hybridoma Frequency[b] | Antigen-Reactive Wells (% positive wells) |
|---|---|---|---|---|
| HAT (−FCS) | 211/384 (55) | 1.2 | $0.4 \times 10^{-4}$ | 19 (9) |
| HAT (−FCS) | 154/384 (40) | 0.8 | $0.3 \times 10^{-4}$ | 23 (15) |
| CFSF (+HT) | 357/384 (93) | 3.9 | $1.3 \times 10^{-4}$ | 146 (41) |
| CFSF (−HT) | 353/364 (97) | 4.5 | $1.5 \times 10^{-4}$ | 205 (58) |

[a]Fusion products were plated at a density corresponding to $3 \cdot 10^4$ NS-1 cells/100 μl/well. Cultures were scored for hybridoma colonies and antigen-reactive antibodies on day 14.
[b]Hybridoma frequencies are expressed with respect to NS-1 cells.

Since the fusion described in Table 1 yielded between 1 and 5 hybridoma colonies per well, the effect of fusion product plating density on hybridoma yields in both CFSF and HAT media (Table 2) were examined. As the plating density of fusion products decreased to $5 \times 10^3$ NS-1 cells per well, the frequencies of hybridomas remained relatively constant in both selection media while the proportions of hybridoma-bearing wells and mean numbers of colonies per well decreased. Under these conditions CFSF medium yielded 5- to 9-times as many hybridomas as HAT medium. At plating densities below $5 \times 10^3$ NS-1 cells per well the recovery of hybridomas decreased markedly such that no hybridomas were recovered in either medium when fusion products were plated at $1 \times 10^3$ NS-1 cells per well. In both media the proportion of A431-reactive wells decreased with decreasing plating densities of fusion products; this decrease probably reflected the reduction in mean numbers of hybridoma colonies per well. However, at each plating density 3- to 13-times as many antigen-reactive wells were obtained with CFSF medium as with HAT medium commensurate with the greater yields of hybridomas in CFSF medium.

TABLE 2

Effects of Fusion Product Density on Hybridoma Growth[a]

| Seeding Density[b] | Positive Wells (%) | Mean Colonies/Well | Hybridoma Frequency[b] | Antigen-Reactive Wells (% positive wells) |
|---|---|---|---|---|
| $3 \times 10^4$ cells/well | | | | |
| CFSF | 181/183 (99) | 6.2 | $2.1 \times 10^{-4}$ | 109 (60) |
| HAT | 106/188 (56) | 1.2 | $0.4 \times 10^{-4}$ | 32 (30) |
| $2 \times 10^4$ cells/well | | | | |
| CFSF | 170/177 (96) | 5.2 | $2.6 \times 10^{-4}$ | 91 (54) |
| HAT | 78/192 (41) | 0.7 | $0.4 \times 10^{-4}$ | 7 (9) |
| $1 \times 10^4$ cells/well | | | | |
| CFSF | 153/184 (83) | 2.8 | $2.8 \times 10^{-4}$ | 37 (24) |
| HAT | 51/192 (27) | 0.3 | $0.3 \times 10^{-4}$ | 4 (8) |
| $5 \times 10^3$ cells/well | | | | |
| CFSF | 69/192 (36) | 0.6 | $1.2 \times 10^{-4}$ | 14 (20) |
| HAT | 23/192 (12) | 0.1 | $0.2 \times 10^{-4}$ | 3 (13) |
| $3 \times 10^3$ cells/well | | | | |
| CFSF | 4/192 (2) | 0.03 | $1.0 \times 10^{-7}$ | 0 (0) |
| HAT | 4/192 (2) | 0.03 | $1.0 \times 10^{-7}$ | 0 (0) |
| $1 \times 10^3$ cells/well | | | | |
| CFSF | 0/192 (0) | 0 | 0 | 0 (0) |
| HAT | 0/192 (0) | 0 | 0 | 0 (0) |

[a]Fusion products were plated in CFSF medium or HAT medium containing 10% FCS. Wells were analyzed on day 14.
[b]Seeding densities and hybridoma frequencies are expressed with respect to NS-1 cells.

Figure 1:
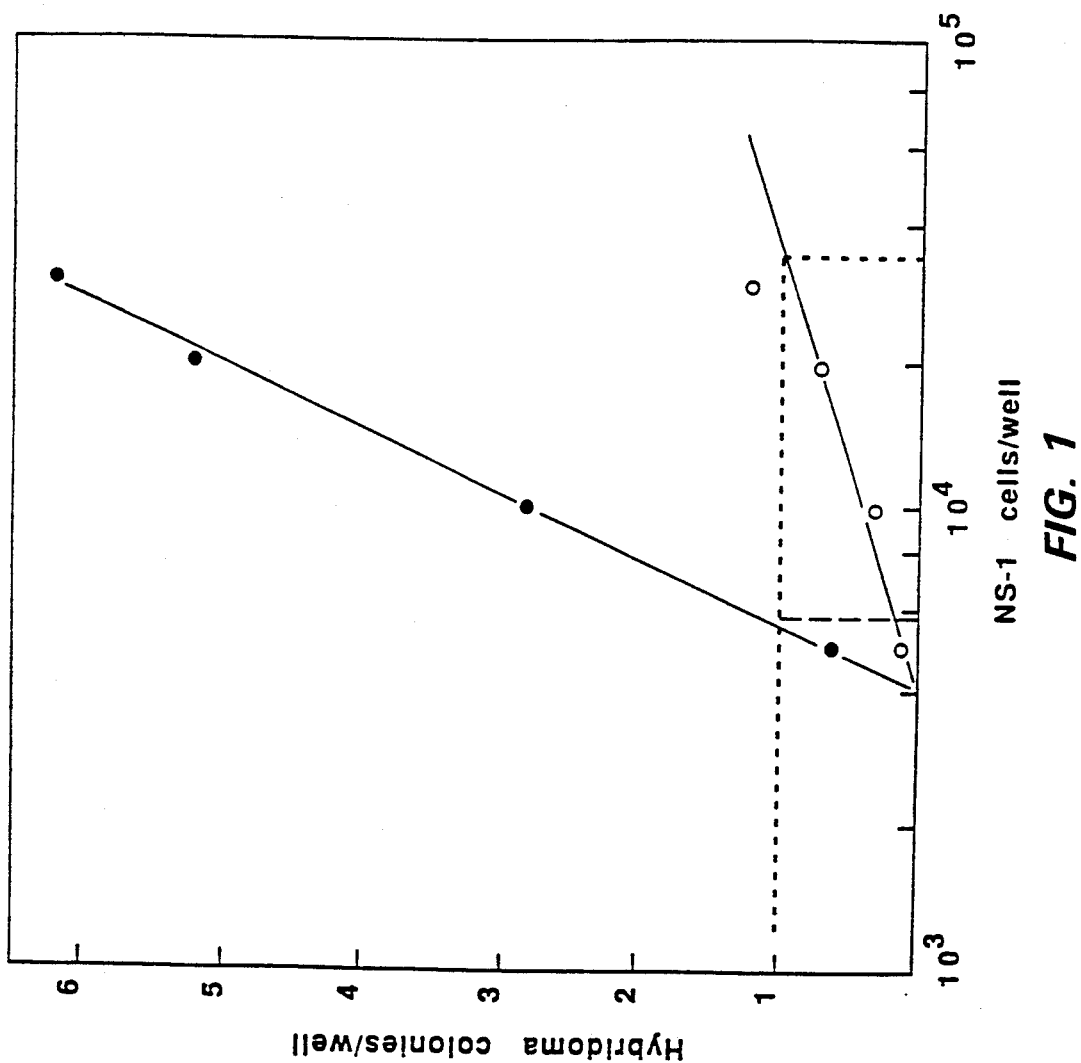
FIG. 1 illustrates the relationship between fusion product seeding density and hybridoma colony formation. Fusion products were plated at various densities in either CFSF medium (•) or HAT medium (o). Hybridoma colonies were counted after 14 days.

FIG. 1 depicts the relationship between fusion product seeding densities, expressed in terms of NS-1 myeloma cells, and the frequencies of hybridoma colonies in both selective media: an average of one colony per well was recovered in CFSF medium at a seeding density of $6 \times 10^3$ NS-1 cells per well while $3.5 \times 10^4$ NS-1 cells were necessary to generate one hybridoma colony per well in HAT medium; extrapolation to the abscissa indicated that no colonies could be recovered in either medium at NS-1 seeding densities below $4 \times 10^3$ cells per well. These results demonstrated that CFSF medium was superior to HAT medium in promoting the outgrowth of nascent hybridomas and was more effective than HAT medium for cloning hybridomas.

Figure 2:
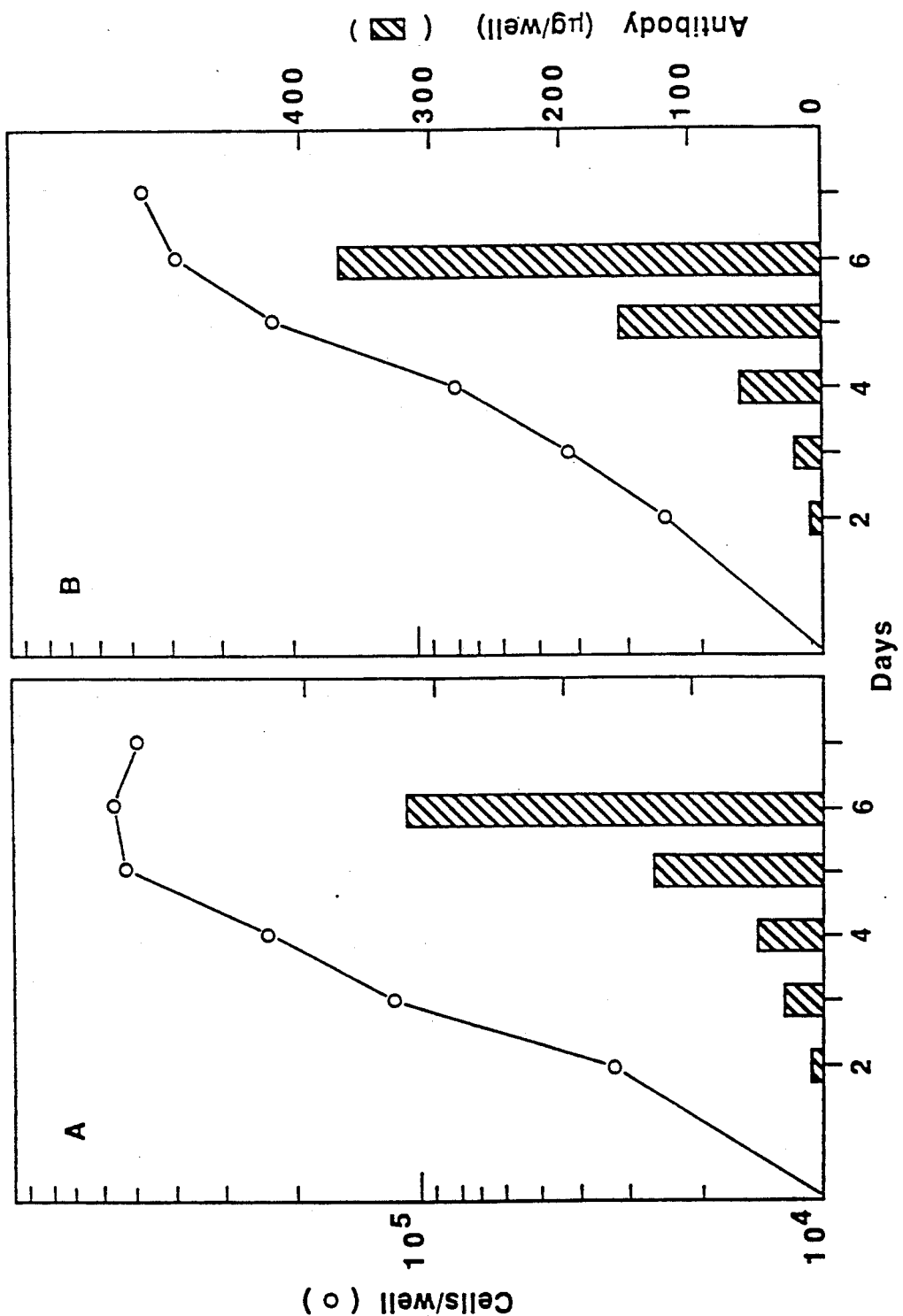
FIG. 2 illustrates the growth and antibody production by hybridomas in CFSF medium. Hybridomas 10-77 (A) and 12-93 (B) were plated at $10^4$ cells/ml in CFSF medium. The cells in duplicate wells were counted and culture media were assayed by ELISA for antibodies on the indicated days.

The growth kinetics and antibody production of two representative hybridomas, 12-93 and 10-77, that were obtained by CFSF-selection were examined. Both hybridomas secreted antibodies to epidermal growth factor receptors (data not shown). As shown in FIG. 2, hybridoma 12-93 doubled every 14 hours and produced IgG$_1$ antibody at a rate of 470 μg/well per $10^6$ cells per day in CFSF medium. Hybridoma 10-77 doubled every 13 hours and produced IgM antibody at a rate of 200 μg/well per 10% cells per day. In addition the growth of these CFSF-selected hybridomas was inhibited by fetal calf serum.

The mouse myeloma cell lines NS-1, P3-X63-Ag8 and X63Ag8.653 are unable to synthesize cholesterol owing to a deficiency in 3-ketosteroid reductase activity. Thus, these cells require exogenous cholesterol or cholesterol precursors downstream from 3ketosteroid ketosteroid reductase, such as lathosterol or desmosterol, for survival and growth in serum-free medium. Although cholesterolindependent variants of these cells can be selected after prolonged growth in low concentrations of serum, this phenotype of cholesterol auxotrophy is very stable.

The above-described results demonstrate that the sterolrequirement of NS-1 cells can be exploited to select NS-1 hybridomas under cholesterol-free culture conditions. When compared with HAT-selection of hybridomas, CFSF-selection yielded 3- to 9fold higher frequencies of hybridomas and 3- to 13-fold as many antigen-reactive hybridoma wells. Together, these results indicate that the polyethylene glycol-mediated cell fusion protocol did not induce cholesterol-independence in NS-1 cells and that CFSF medium was more efficient in supporting the growth of nascent hybridomas. The greater efficacy of CFSF medium is further supported by the observation that a 6-fold higher fusion product density was required in HAT medium to achieve an average of one hybridoma colony per well (FIG. 1). Although CFSF-selection has only been applied to the derivation of NS-1 hybridomas in this study, it is clear that this alternative to HAT-selection can be used to select hybridomas derived from any cholesterol-dependent mammal, such as mouse or human, parent cell line.

(3) EXPERIMENTAL METHODS

Exmperiment 1a

NS-1 cells were plated at $1 \times 10^4$ cells/well in the following media: RD, RPMI 1640, DME and F-12.

To each medium were added: transferrin, insulin, ethanolamine, mercaptoethanol, selenium and low density lipoprotein (LDL). LDL is used to supply cholesterol, without which these cells die. The seeding density was $1 \times 10^4$ cells/well.

The cells were grown for 126 hours, and then counted. The results are expressed as cells/well and as percent growth with RD medium set as 100%.

The results of Experiment 1 are illustrated in FIG. 3. Relative to growth in RD medium, cell growth was decreased in RPMI 1640 and DME, but the cells died in F-12 medium such that fewer cells were recovered at the end of the experiment than were originally put in the wells. The final number of cells in F-12 medium was 2% of the cells recovered from RD medium at the end of the experiment.

Experiments 1(b) and 1(c)

Experiment 1(a) was repeated using NS-hybridomas 455 [Experiment 1(b)]and 528 [Experiment 1(c)]. The seeding densities were $1 \times 10^4$ cells/well. Cells were grown for 112 hrs. The results are shown in FIGS. 4 and 5.

Experiments 2 and 3

NS-1 cells were plated at $5 \times 10^3$ cells/well in RD medium or RDF (1:1:1) medium. The seeding density was $5 \times 10^3$ cells/well.

Transfectin, insulin, ethanolamine, mercaptoethanol, selenium and LDL were added to the media as in Experiment 1. The cells were counted periodically over eight days.

The results are shown in FIGS. 6 and 7. In both experiments the growth rate of the cells, expressed as doubling time (Td; the time in hours for the cell population to double in number), decreased in RDF medium.

That is, the length of the doubling time increased relative to the Td in RD medium.

From the results of these experiments, it can be concluded that F-12 medium alone is toxic to NS-1 cells, and it inhibits NS-1 growth when added to RD medium. This toxicity would be expected to decrease the yield of hybridomas from NS-1 parent cells in selection mediums containing F-12. Since strong growth of such hybridomas surprisingly occurs in the absence of F-12, the inclusion of F-12 in the selection medium is undesirable.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology and terminology employed herein is for the purpose of description and not of limitation.

What is claimed is:

1. A method for selecting mammalian derived hybridoma cells, which are the fusion product of a myeloma cell, which is a cholesterol auxotroph due to the deficiency of an essential enzyme in the metabolic pathway of cholesterol production, and a cell which is capable of synthesizing cholesterol and which maintains this characteristic after fusion with the myeloma cell, from unfused parent myeloma cells, comprising the step of culturing a mixture of said hybridoma cells and said unfused parent myeloma cells in a nutrient medium suitable for the growth of said hybridomas, said medium lacking cholesterol and cholesterol precursors downstream from the deficient essential enzyme of the myeloma cells in amounts sufficient to support significant growth of said myeloma cells, whereby said hybridoma cells grow and said unfused parent myeloma cells die.

2. A method in accordance with claim 1, wherein said nutrient medium consists essentially of a 1:1 mixture by volume of RPMI 1640 and high glucose Dulbecco's modified Eagle's medium with 5 micrograms/ml crystalline bovine insulin, 5 μg/ml $Fe^{3+}$-free human transferrin, 10 μM mercaptoethanol, 10 μM 2-aminoethanol, 10 nM sodium selenite, 15 mM Hepes buffer, 0.01% sodium pyruvate, 2.2 g/l sodium bicarbonate and an amount of antibiotic effective to prevent bacterial infection of said culture.

3. A method in accordance with claim 1, wherein said unfused parent myeloma cells are NS-1 cells.

4. A method in accordance with claim 1, wherein said cell which is the fusion partner of the myeloma cell is an antibody producing cell.

5. A method in accordance with claim 1, wherein said hybridomas are the product of fusion of normal mammalian spleen cells with NS-1 myeloma cells.

6. A method in accordance with claim 5, wherein said spleen cells are murine spleen cells.

7. A method in accordance with claim 6, wherein said spleen cells are obtained from a BALB/c mouse.

8. A method in accordance with claim 1, wherein said myeloma parent cells are from the cell line NS-1-Ag4-1.

9. A method in accordance with claim 1, wherein said nutrient medium is further essentially free of Ham's F-12 nutrient mixture.

10. A method in accordance with claim 1, wherein said myeloma cell is one in which the cholesterol auxotroph is due to a deficiency of 3-ketosteroid reductase.

11. A method in accordance with claim 1, wherein said nutrient medium contains Fe, Cu and Zn at a concentration below the level of Fe, Cu and Zn in Ham's F-12 nutrient mixture, said concentation of Fe, Cu and Zn not being inhibitory to the growth of said hybrodima cells.

* * * * *